(12) United States Patent
Pisanello et al.

(10) Patent No.: US 11,696,689 B2
(45) Date of Patent: Jul. 11, 2023

(54) SYSTEM AND METHOD FOR AXIALLY RESOLVED LIGHT COLLECTION FROM A TAPERED WAVEGUIDE

(71) Applicants: FONDAZIONE ISTITUTO ITALIANO DI TECNOLOGIA, Genoa (IT); PRESIDENT AND FELLOWS OF HARVARD COLLEGE, Cambridge, MA (US)

(72) Inventors: Ferruccio Pisanello, Lecce (IT); Marco Pisanello, Alliste (IT); Leonardo Sileo, Calimera (IT); Bernardo L. Sabatini, Newton, MA (US); Massimo De Vittorio, Lecce (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 746 days.

(21) Appl. No.: 16/493,938

(22) PCT Filed: Mar. 14, 2018

(86) PCT No.: PCT/IB2018/051699
§ 371 (c)(1),
(2) Date: Sep. 13, 2019

(87) PCT Pub. No.: WO2018/167685
PCT Pub. Date: Sep. 20, 2018

(65) Prior Publication Data
US 2020/0138296 A1    May 7, 2020

(30) Foreign Application Priority Data
Mar. 15, 2017 (IT) .................. 102017000028787

(51) Int. Cl.
*A61B 5/00* (2006.01)

(52) U.S. Cl.
CPC .......... *A61B 5/0075* (2013.01); *A61B 5/0084* (2013.01)

(58) Field of Classification Search
CPC .................................................. A61B 5/0075
See application file for complete search history.

(56) References Cited

U.S. PATENT DOCUMENTS 10,398,293 B2 * 9/2019 Pisanello ................. A61B 1/07
2013/0030274 A1 * 1/2013 Jamieson .............. A61B 5/0084
600/377

(Continued)

FOREIGN PATENT DOCUMENTS

EP           3 021 738           9/2017
WO   WO-2015008233 A1 *   1/2015 ............... A61B 1/07

OTHER PUBLICATIONS

Guo et al. "Multi-channel fiber photometry for population neuronal activity recording" Biomedical Optics Express 3919 vol. 6, No. 10, Sep. 2015. (Year: 2015).*

(Continued)

*Primary Examiner* — Joseph M Santos Rodriguez
(74) *Attorney, Agent, or Firm* — Valauskas Corder LLC

(57) ABSTRACT

A system for optical spectroscopy through a probe implanted in a tissue is provided. The system includes a light collecting probe comprising a waveguide formed by a single optical fiber and having a proximal end and a distal end, the proximal end being formed with a taper along which at least one optical window is positioned, wherein light entering at an axial section of the taper generates a specific subset of guided modes defined by the diameter of the single optical fiber at the axial section, the guided modes propagating toward the distal end of the waveguide and generating an output at the distal end of the waveguide; a demultiplexer configured to receive outputs provided by the light collect- (Continued)

ing probe and discriminate the outputs based on their modal content of origin; and a detector configured to detect the discriminated outputs.

22 Claims, 6 Drawing Sheets

(56) References Cited

U.S. PATENT DOCUMENTS

2016/0157706 A1* 6/2016 Pisanello ............... A61N 5/062
            604/20
2016/0268764 A1* 9/2016 Giessen ............ H01S 3/094076

OTHER PUBLICATIONS

Pisanello, Marco et al. Modal Demultiplexing Properties of Tapered and Nanostructured Optical Fibers for In Vivo Dptogenetic Control of Neural Activity. Biomedical Optics Express; 6(10): 4014-26. Sep. 17, 2015.

Pisanello, Ferruccio et al. Multipoint-Emitting Optical Fibers for Spatially Addressable In Vivo Optogenetics. Neuron; 82(6): 1245-54. Jun. 18, 2014.

* cited by examiner

SYSTEM AND METHOD FOR AXIALLY RESOLVED LIGHT COLLECTION FROM A TAPERED WAVEGUIDE

STATEMENT AS TO RIGHTS TO INVENTIONS MADE UNDER FEDERALLY SPONSORED RESEARCH OR DEVELOPMENT

This invention was made with United States Government support under NS094190 awarded by the National Institutes of Health. The United States Government has certain rights in this invention.

CROSS-REFERENCE TO RELATED APPLICATIONS

This application is a U.S. National Phase filing of PCT International Patent Application No. PCT/IB2018/051699, having an international filing date of Mar. 14, 2018, which claims priority to Italian Patent Application No. 102017000028787, filed Mar. 15, 2017 each of which is hereby incorporated by reference in its entirety.

FILED OF THE INVENTION

The present invention relates to the techniques for in tissue optical spectroscopy.

BACKGROUND OF THE INVENTION

Optical spectroscopy comprises several techniques (fluorescence spectroscopy, reflectance spectroscopy, Raman spectroscopy), which are increasingly employed as a source of information for structural, functional and diagnostic analysis of the living tissue. However, there is a general limitation of existing technologies to gather out light signal from deep tissues: the tissue itself is an opaque medium and generated photons are commonly absorbed or scattered before reaching the light collecting device, in particular when generated far away from it. This translates in an overall difficulty in assessing the depth at which fluorescence is generated, and existing methods such as two-photon microscopy or optical fiber bundles are limited to depths of a few hundreds of micrometers. Therefore, development of devices able to discriminate the depth at which light signal is generated in the range of several millimeters, represents a main target for both research and clinical devices, and would greatly boost both basic science and diagnostic methods.

For illustrative purposes only, two main fields of in vivo optical spectroscopy are discussed here: (i) fluorescence spectroscopy for diagnosis of tumoral tissues, and (ii) fiber photometry for neurobiology studies in deep brain regions.

Application (i) is mainly driven by clinical studies in different tissues (neck, cervix, skin, bladder, bronchus, esophagus, colon, breast, brain, and artery) that reported the possibility of using fluorescence spectroscopy of tissue autofluorescence to discriminate between normal and tumorigenic tissues in vivo in humans, with major fluorescence contribution coming from structural proteins differentially present in the two type of tissue such as elastin and collagen, pyridine nucleotide, flavoprotein, tryptophan, and porphyrins. To detect autofluorescence from tissue, most of the published studies are based on fiber optic probes used as endoscopes (and often based on existing endoscopic equipment) to investigate cavities and hollow organs. When applied in vivo in patients, these studies relate on setups for steady state measurements, allowing to measure intensity and/or the spectral content of the signal in a relatively simple and inexpensive way. However, obtaining absolute values of the light emission intensity results to be difficult, due to changes in light excitation-collection geometries caused by tissue movements, endogenous absorbers (e.g. hemoglobin) and photobleaching effects. Specificity of fluorescence detection can be improved by lifetime measurements of collected fluorescence, which do not depend on fluorophores concentrations. In this case, the contrast mechanism relies on the dependence of fluorescence decay times on the physicochemical properties of the environment (temperature, pH, enzymatic activity, ion concentration), which are different in normal and abnormal tissue.

To measure autofluorescence and therefore to extrapolate the abovementioned figures of merit, research and commercial systems have been realized either for single point or multi-point measurements of fluorescence in vivo. Devices for collecting fluorescence signals from a single point (both for steady-state and life-time measurements) commonly consist of one optical fiber used to excite the autofluorescence accompanied by multiple collection fibers, since single-fiber approaches are affected by low signal-to-noise ratios due to autofluorescence of impurities in the fiber core and to specular reflection from the fiber surface. Probes for multi-point measurements, instead, consist of an arrangement of multiple single-point probes, with a consequent large size implant. A more compact solution, having a circular implant cross section of a few hundreds of micrometers in diameter, relies on the use of a fiber bundle, a particular type of optical fiber having hundreds to thousands of very small size cores embedded in a shared cladding matrix. It is commonly coupled to a graded-index lens objective and to an imaging system (microscope objective plus a CCD camera) to retrieve an image of the tissue, and is usually classified as microendoscopic imaging. This approach strongly improves resolution down to the cellular level, at the price of a reduced field of view and increased complexity and cost of instrumentation. However, it only allows for an image on a plane and can hardly discriminate fluorescence depths above a few hundreds of micrometers below its surface.

Indeed, the endoscopic fiber probes employed in any of the above mentioned fiber optic systems are designed for use in contact or in close proximity of the volume of tissue to be investigated. The information obtained is related to a volume of tissue determined by the absorption and scattering properties of the tissue itself. For instance, when analyzing epithelial tissue, most of the signal actually comes from the underlying connective tissue (stroma) masking the useful information carried by the autofluorescence of the epithelium about the existence of a precancerous or cancerous lesion. Since the majority of cancers originate in the epithelial tissue, it is mandatory to be able to separate the epithelial and stroma fluorescence, that translate in the need for a depth-resolved fluorescence detection system. One approach to obtain a depth-resolved measurement of tissue autofluorescence is the use of two fibers, one for illumination and one for light collection. It is based on an optical scheme in which fluorescence is collected only at a depth proportional to the spatial separation between illumination and collection site. However, in the specific case of epithelial tissue, the signal from the stroma tends to dominate even at minimum source-detector separation. Another approach is to use an angled illumination fiber-optic probe. Also in this case, the approach finds a physical limit when designed to target the superficial epithelium (too large bevel angles reduce collection efficiency). Other strategies include variation of the diameters of the illumination and collection fibers, or more recently the use of lensed single or dual-fiber probes. In all these approaches, the depth of the tissue from which the signal is most efficiently and selectively collected depends on probe geometry (which is fixed) and on tissue optical properties (which are variable and can only be estimated as average values) and cannot be exactly determined, thus affecting depth resolution capability.

Therefore, although this field would greatly benefit of depth-resolved light-collection systems, none of the existing approaches allows for an efficient estimation of light-source depth and cannot probe tissue depths above 1 millimeter. Moreover, existing technologies are often quite invasive and based on multiple implanted optical waveguides.

As mentioned above, a second field of application is related to neurobiology studies in deep brain regions, exploiting a technique referred to as fiber photometry, which can be regarded as a particular case of fiber optic fluorescence spectroscopy. It refers to the collection of fluorescence signal through an optical fiber implanted in the brain in close proximity to a region where fluorescent indicators of neuronal activity or indicators of cytotypes are expressed by genetic engineering techniques. In the classical implementation of fiber photometry the observed neuronal populations express genetically encoded fluorescent indicators of calcium concentration or of neurons membrane voltage transients. An optical fiber is used to excite their fluorescence and the fluorescence is collected through the same or another optical fiber. Photons are collected in the form of a time-varying signal indicating the collective activity of the subset of neurons expressing the fluorescent indicator of neural activity. In more advanced schemes, the same cellular population can express also light-gated ion channels or pumps, to allow also a control of neural activity with the same or different light radiation. Even in this relatively simple implementation, fiber photometry is recognized of great importance for developing closed loop optogenetics applications both for behavioral studies and for clinical applications. More in general, fiber photometry is regarded as a less invasive, lower cost tool to read out neuronal activity with respect to microendoscopic imaging, which is mostly based on fiber bundles and microobjectives.

Approaches for multipoint fiber photometry in the living brain have been recently presented based on the use of multiple-fiber patch-cords, tightly bundled on one end and split into separate branches on the other end. In one case, a scanning system coupled to an objective alternatively sends light to and collect fluorescence from one of the fibers. One photodetector is used to detect the fluorescence from all the fiber cores and time-division multiplexing is employed to separate the signals. In another application, all the fibers are involved at the same time for light delivery and collection and a sCMOS camera simultaneously measures fluorescence signal from all the fibers.

The microendoscopic imaging approach has also been applied for brain studies.

Also in this second field of application, existing technologies are limited to fluorescence signal which is only a few hundreds of micrometers away from the implanted optical fiber and only multiphoton microscopy can approach depths close to 1 mm, but it is limited by the fact the microscope objective must stay outside the brain and deep-brain structures are therefore not accessible with spatial resolution and simultaneous minimum invasiveness by existing technologies.

SUMMARY OF THE INVENTION

One aim of the invention is to provide a system for in tissue depth-resolved optical spectroscopy based on a minimally invasive probe.

In accordance with this aim, the invention proposes a system for optical spectroscopy through a probe implanted in a tissue, said system including
  a light collecting probe comprising a waveguide formed by a single optical fiber and having a proximal end and a distal end, said proximal end being formed with a taper along which at least one optical window is positioned, wherein light entering an axial section of the taper generates a specific subset of guided modes defined by the diameter of the fiber at that axial section, said guided modes propagating toward the distal end of the waveguide and generating an output at the distal end of the waveguide;
  a demultiplexer configured to receive outputs provided by the probe and discriminate said outputs based on their modal content of origin; and
  a detector configured to detect the discriminated outputs.

The system according to the invention is conceived for collecting fluorescence and/or scattering signals (either endogenous or exogenous) from a living tissue in which the tapered waveguide has been implanted with minimized invasiveness. Depending on the section at which light is collected by the taper, different subsets of guided modes are generated into the fiber. The taper itself therefore operates as a mode division multiplexer. A readout optical system comprising demultiplexing and detecting functions is designed for discriminating the signal gathered by different sub-sections and operates as a mode division demultiplexer, allowing for depth-resolved fluorescence spectroscopy from a total depth of up to several millimeters.

As used herein, the term "implanted" does not mean necessarily that the probe is implanted in a human or animal body. According to embodiments of the invention, the probe can be implanted in an ex vivo or in vitro tissue.

A further object of the invention is a method for optical spectroscopy through a probe pre-implanted in a tissue, said probe comprising a waveguide formed by a single optical fiber and having a proximal end and a distal end, said proximal end being formed with a taper along which at least one optical window is positioned,
  wherein said method comprises
  collecting light through the probe, wherein light entering an axial section of the taper generates a specific subset of guided modes defined by the diameter of the fiber at that axial section, said guided modes propagating toward the distal end of the waveguide and generating an output at the distal end of the waveguide;
  receiving outputs provided by the probe and discriminating said outputs based on their modal content of origin; and
  detecting the discriminated outputs.

Some advantages of the disclosed system and method are summarized hereinbelow:
  In-depth light collection: the system and method allow for the acquisition of signals from a total depth of up to several millimeters with the proper detection system. This is possible thanks to the properties of waveguide, which is able to collect light all along the tapered region.
  Minimized invasiveness: thanks to the properties of the taper and of the coupled detection system, the system and method allow for multi-point light collection with a single waveguide. It is therefore possible to acquire information from deep regions of tissues while minimizing the invasiveness.

High axial resolution: the axial resolution is granted by the unconventional exploitation of the physics of light propagation into a tapered optical fiber. Indeed, the number of guided modes sustained by the taper decreases as the section of the taper decreases. Depending on where the light enters into the taper, only a subset of guided modes back-propagates to the distal end. Moreover, within this modal subset, only the modes which are characterized by a high transversal component of the wavevector $k_t$ better couple with the radiation into the environment. Therefore, it is possible to assign a specific input point to the detected light radiation based on the readout of light intensity at different $k_t$. Lastly, the resolution can be improved or reduced, according to the specific application, depending on the overall structural and optical properties of the taper (numerical aperture of the non-taper fiber region, taper angle, eventual metal masking).

Tunability and versatility: as already mentioned, depth range and resolution can be adjusted according to the specific needs. However, it is also important to note the versatility of the system and method: indeed, they work well with both a pure dielectric waveguide (continuous input points along the fiber) and a metal-coated waveguide with small collecting openings (discrete input points). Furthermore, the system and method can be extended to cases where the light is not self-generated in the environment. A secondary radiation may be introduced through the same waveguide (exploiting the light-delivery properties of the taper), by integrating light generators directly along the fiber or by means of an external device.

Even if the invention has been conceived particularly for in vivo applications, it can be used for ex vivo or in vitro applications as well.

BRIEF DESCRIPTION OF THE DRAWINGS

Further characteristics and advantages of the proposed device will be presented in the following detailed description, which refers to the attached drawings, provided purely by way of non-limiting example, in which.

DETAILED DESCRIPTION

Figure 1:
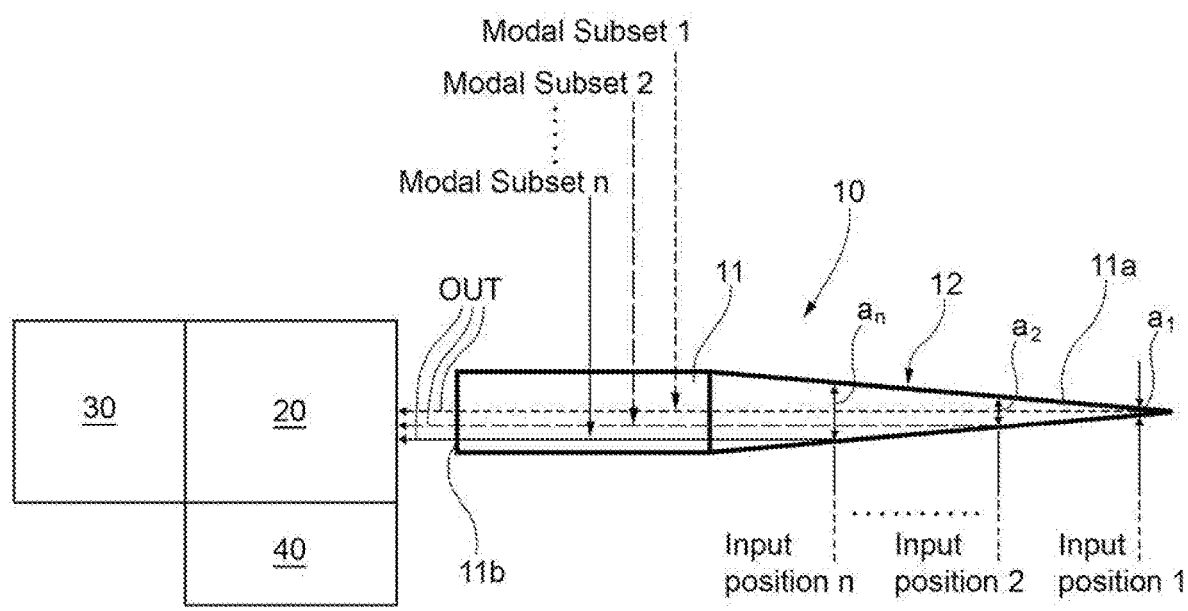
FIG. 1 is a principle diagram of a fiber-photometry tool according to the invention. An optical fiber collects light along a tapered region, acting as a mode-division multiplexer to allow for discrimination of signals collected at different sections of the taper. This is done through a demultiplexer module used in combination with an appropriate detector and/or light delivery module.

FIG. 1 schematically shows a system for optical spectroscopy through a probe pre-implanted in a tissue (not shown). The implantation step does not form part of the present invention.

Figure 2:
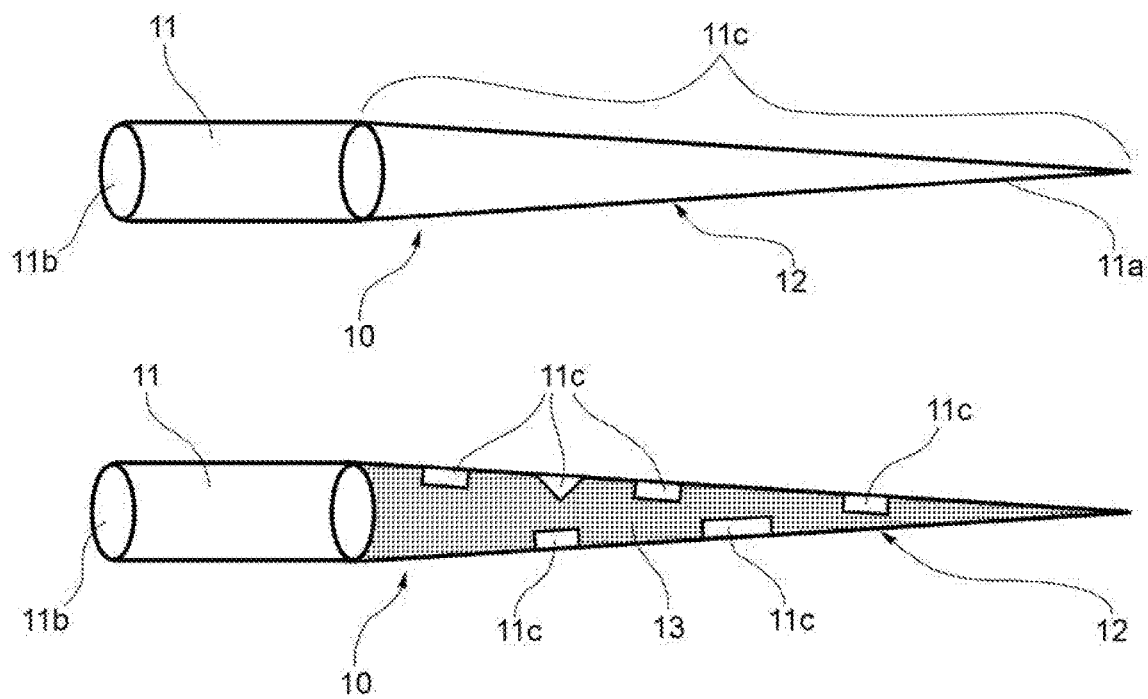
FIG. 2 shows two possible configurations of the fiber taper: a dielectric waveguide with continuously distributed input points (top panel A) and a metal-coated waveguide with discrete input sections (bottom panel B)

The system comprises a light collecting probe 10 comprising a waveguide 11 formed by a single optical fiber. The waveguide 11 has a proximal end 11a and a distal end 11b. The proximal end 11a is formed with a taper 12 along which at least one optical window 11c (see FIG. 2) is positioned. Light entering at an axial section of the taper 12 generates a specific subset of guided modes defined by the diameter of the optical fiber at that axial section. These guided modes propagate toward the distal end 11b of the waveguide 11 and therefore generate an output OUT at the distal end 11b of the waveguide 11.

Furthermore, the system comprises a demultiplexer module 20 configured to receive outputs OUT provided by the probe 10 and discriminate said outputs based on their modal content of origin, as well as at least one detector module 30 configured to detect the discriminated outputs. The system may also comprise at least one light delivery module 40.

The probe 10 is based on the photonic properties of the tapered end of an optical fiber. It collects light at different positions along and/or around the taper axis, and the taper itself generates a correspondence between the input points and the subsets of guided modes propagating toward the distal end of the optical fiber. Therefore, the taper operates as an optical mode division multiplexer. The demultiplexing system 20 can then be employed to readout this correspondence by using one or more detectors 30, associating a light intensity value to each input position.

The operating principle of the tool is founded on an unconventional exploitation of the physics of light propagation into a tapered optical fiber. For sake of simplicity, the following description takes into account n input positions distributed along the taper, as shown in FIG. 1. Depending on where light enters into the taper 12, different subsets of guided modes are generated toward the distal end 11b of the fiber 11. This is obtained because the number of guided modes $N_i$ sustained by the taper 12 at the i-th section of diameter $a_i$ decreases as the waveguide diameter decreases, e.g. $N_a > \ldots > N_i > \ldots > N_2 > N_1$, with $a_a > \ldots > a_i > \ldots > a_2 > a_1$. If $S_i$ represents the set of guided modes at the i-th section, this implies that $S_1 \subset S_2 \subset \ldots \subset S_i \subset \ldots \subset S_{n-1} \subset S_n$. Within the modal subset $S_i$, for each propagating mode (here referred by the generic index j) one can identify a transversal and an axial component of the wavevector, $k_{j,t}$ and $k_{j,a}$, respectively, for which the relation $k_0^2 = k_{j,t}^2 + k_{j,a}^2$ holds true (with $k_0 = 2\pi n/\lambda$, n the refractive index of the waveguide and $\lambda$ the free-space wavelength). In general, guided modes with high $k_{j,t}$ better couple with the radiation into the environment with respect to modes with a small $k_{j,t}$. Therefore, at the i-th section only some of the modes into the subset $S_i$ can couple well with the radiation into the environment. Those modes are characterized by a high $k_{j,t}$ component and are mostly those not allowed to propagate at section i−1, at which they become radiative. Consequently, light entering the taper at the section i-th back-propagates toward the distal end 11b of the fiber mainly within the modal subset $S_i$-$S_{i-1}$, thus exploiting a peculiar property of the fiber taper. A modal demultiplexing scheme, based on the readout of the light intensity at different $k_{j,t}$ emerging from the distal facet 11b of the optical fiber, can be used to assign a specific input point 11c to the detected light radiation at the distal end 11b of the fiber.

Although the present disclosure uses a notation based on the discrete index i, the approach works well for both continuous and discrete input points along the fiber taper 12 (see experimental demonstration discussed in the following). Continuously distributed input points along the taper 12 can be obtained, for instance, with pure dielectric waveguides (see FIG. 2.A), while discrete collection points can be obtained by using a reflecting mask around the taper 12 with small openings operating as collection windows 11c (see FIG. 2.B).

Figure 3:
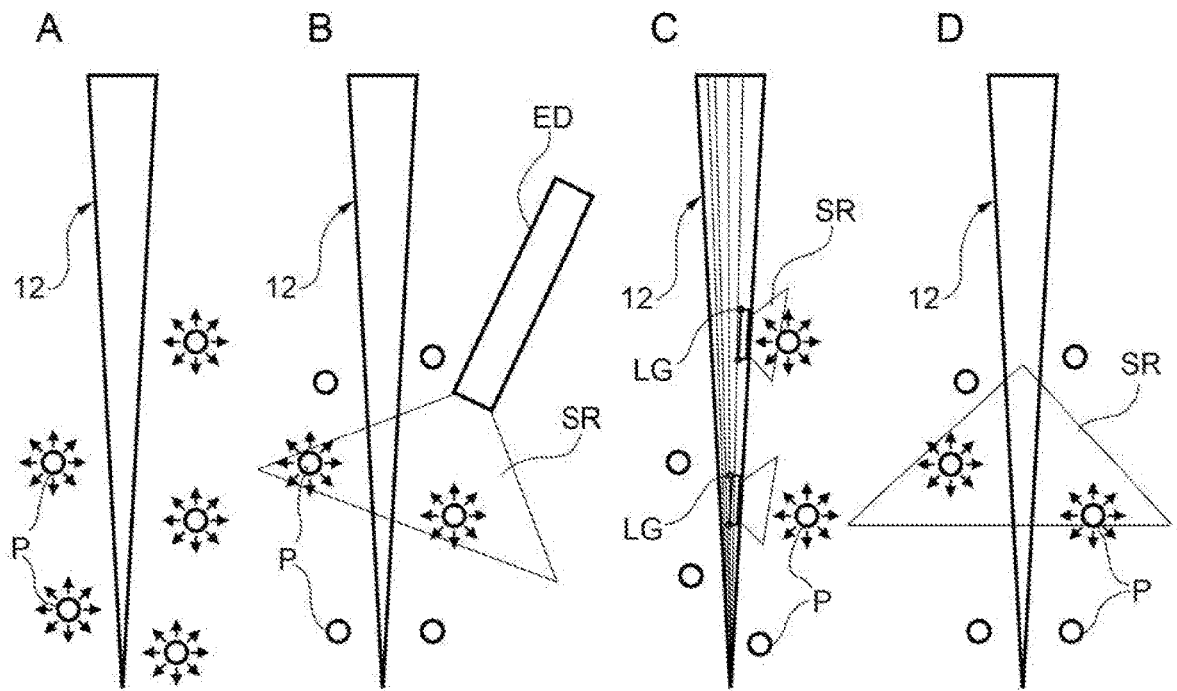
FIG. 3 shows different embodiments in which light in the environment can be self-generated (Panel A) or emitted as a response to a second radiation (panels B-D). (Panel B) Secondary radiation introduced by an external device. (Panel C) Secondary radiation introduced by devices carried by the fiber taper. (Panel D) Secondary radiation guided and delivered by the here-proposed device.

With reference to FIGS. 3.A-3.D, a probe is shown which is inserted in a tissue. The dots P represent different points in different positions of the tissue or environment. Light coming from the tissue or environment is represented by small arrows radially extending from certain dots P.

The light in the environment, which is collected by the tapered device, can be: (i) self-generated by light sources P in the environment (FIG. 3.A), such as in the case of auto-luminescent materials, or (ii) emitted or scattered as a response to a secondary radiation SR (see FIGS. 3.B, C and D). The secondary radiation SR can be of any type able to generate the optical signal that is collected through the tapered waveguide (this is possible, for instance, with optical, thermal, magnetic, acoustic radiation). It can be introduced into the environment by an external device ED (FIG. 3.B) or also by the same tapered optical fiber which is used to collect light. This latter configuration can be achieved by integrating light-generators LG directly along the fiber (such as micro light emitting devices, luminescent molecules, colloidal nanocrystals or any suitable electro-luminescent element, see FIG. 3.C), or by exploiting the light-delivery properties of the probe 10 itself (FIG. 3.D) as disclosed in EP 3 021 738 A1, and using a specific light delivery module 40 (see FIG. 1 and description below).

Different assembling of the detectors 30, demultiplexer 20 and light delivery moduli 40 can make the system operating in different modalities, with different complexities and performances in terms of signal-to-noise (SNR) ratio and detection speed. Some possible configurations are summarized in FIGS. 4-6, valid for fiber optics with both continuous and discrete sets of collecting points. In these figures, a collection lens is designated with 51, a dichroic mirror is designated with 52, while the Fourier plane of the collection lens is designated with 53. A focusing lens is designated with 54. An imaging sensor is designated with 61. A rotating mirror is designated with M1. The demultiplexer 20, detector 30 and light delivery 40 are represented by boxes containing the different components disclosed herein.

Figure 4:
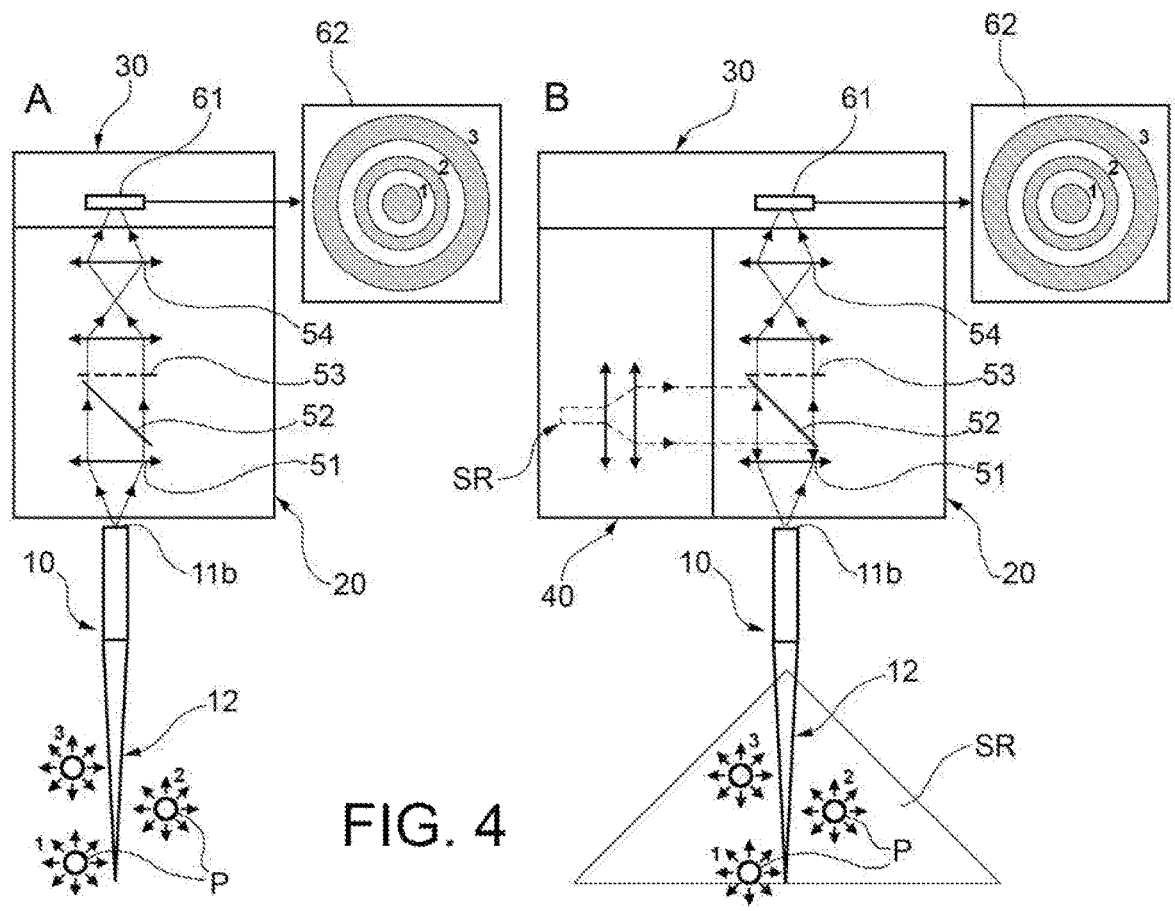
FIG. 4 shows example configurations allowing to simultaneously detect the luminescence of different light sources along the taper and to identify their position. (Panel A) Light collected through the taper is emitted by the fiber back-facet and collected through a collection lens. The Fourier plane of the collection lens is then imaged by two more lenses onto an image sensor, which therefore detect a far-field image of the fiber facet. (Panel B) The same collection scheme illustrated in panel A can be accompanied by a secondary radiation that is delivered in to the environment by the tapered device and allows to generate the luminescence.

The system represented in FIG. 4.A, for instance, is based on a direct measurement of the light intensity associated to the different $k_t$ values generated by the taper 12. An optical system images the far-field radiation [Pisanello et al, Biomedical Optics Express 6, 4014-4026 (2015)] of the fiber output onto an image sensor 61 (a CCD camera or similar). The detected image 62 is represented by a series of concentric rings in the $k_x$-$k_y$ space (x and y defines the plane of the fiber output facet 11b), whose radius is a direct measurement of the $k_t$ values generated by the taper 12 into the optical fiber ($k_t^2 = k_x^2 + k_y^2$), and therefore of the position of light sources P along the taper 12. The integrated intensity of the rings, instead, is a direct measurement of the relative intensity of the different sources P.

If the sources P disposed along the taper 12 need to be excited to deliver the optical signal (fluorescence or scattering), the demultiplexing path in FIG. 4.A can be accompanied by an external source of a secondary radiation SR or by different configurations of the light launching module 40, allowing for different illumination geometries along the taper 12. For this latter case an example light delivery module 40 is represented in FIG. 4.B. It is constituted by an optical system that allows to inject light SR (e.g., from laser source, LED or halogen lamp) into the fiber 11 through the whole acceptance angle defined by the optical fiber numerical aperture, therefore enabling light delivery through the whole taper segment 12 that is allowed to collect light (see FIG. 4.B). With this approach, emission (or scattering) from the different sources along the taper 12 is detected simultaneously, in exactly the same way used in the case in which no secondary radiation is needed (e.g. FIG. 4.A). This scheme, however, could be limited by a cross talk between sources, mainly generated by small amounts of photons collected at taper sections far away from the source itself. With reference to FIG. 4.B, for instance, a few photons generated by source 3 could be collected by taper sections close to source 1, and therefore be misunderstood by the detection system as having been generated by source 1.

Figure 5:
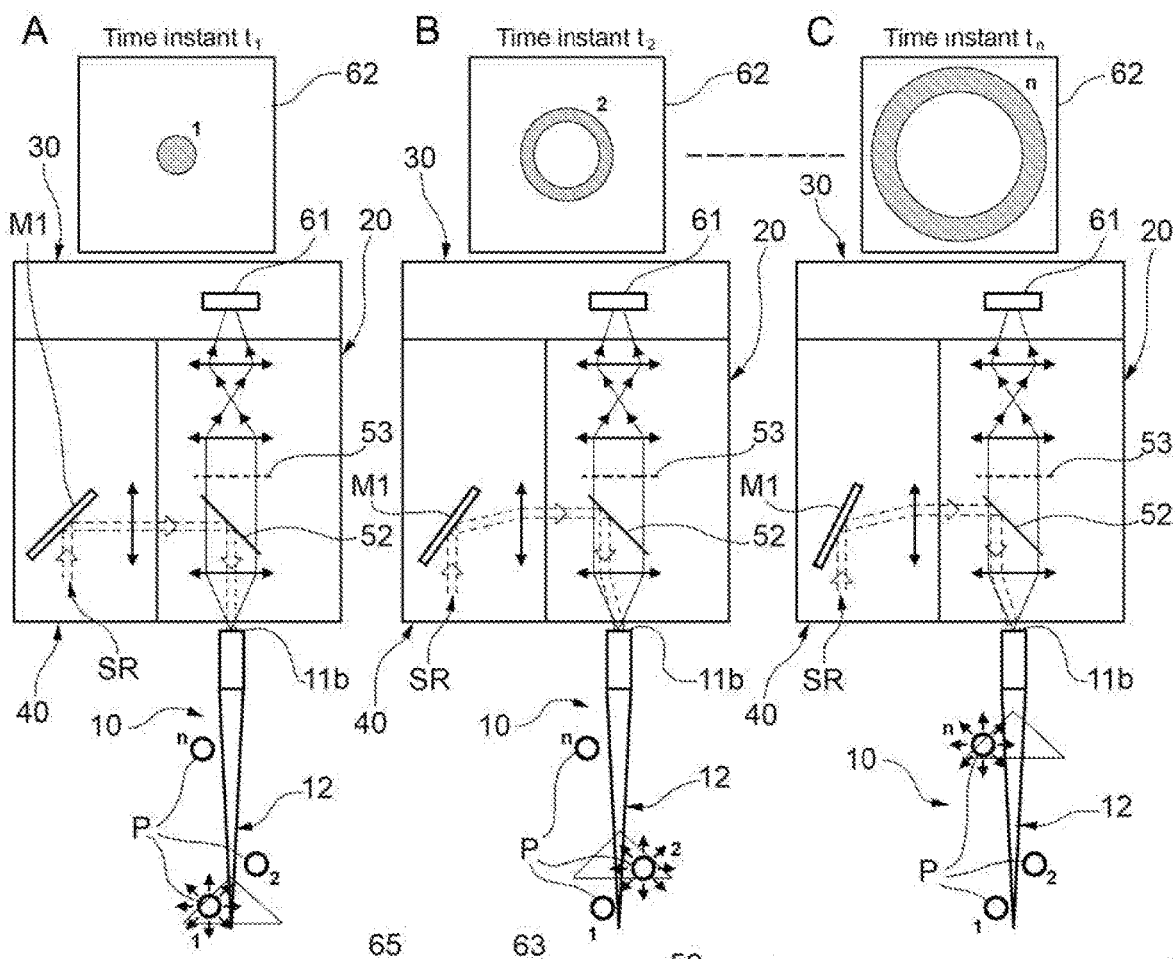
FIG. 5 shows example configurations that allow to sample n sections of the taper in n different time instants (from $t_1$ to $t_n$). Light is injected into the fiber with a very low focusing angle (e.g. much smaller that the fiber numerical aperture) and a defined input angle θ. Depending on θ, light is delivered at different sections of the taper and at each time instant $t_i$ a specific section of the taper is mostly entitled to collect light. When light is detected at the image sensor, only a part of it is exploited to retrieve the luminescence intensity. This part is the one related to the $k_t$ values associated to the section that is entitled to collect light at the specific time instant $t_1$.

To prevent this issue, another light delivery configuration can be used, reported in FIG. 5. In this case the light delivery module shapes the beam SR in order to inject light into the fiber with a defined input angle. A rotating mirror (M1 in FIG. 5) is then used to change this angle and therefore to deliver light through a sub-segment of the taper 12 [Pisanello et al, Neuron 82, 1245-1254 (2014); Pisanello et al, Biomedical Optics Express 6, 4014-4026 (2015); Pisanello et al US 20160157706 A1]. At each mirror's position, fluorescence (or scattering) is generated at a defined and known taper segment, which will be the one mostly entitled to collect light because generated close to it. The excitation beam SR can be moved in time along the taper 12 by rotating mirror M1 and simultaneously collecting photons only with the portion of the image sensor 61 associated to the $k_t$ values that can be detected by the specific section at which light is delivered. This subsampling of the image sensor 61 allows to withdraw photons collected far away from the light delivery section, and the SNR increases. As a consequence, the signal from the different sources is not collected simultaneously, but n sections are sampled during the time instants from $t_1$ to $t_n$.

The rotating mirror M1 can be a standard galvo mirror or a resonant galvo mirror, that allows to improve detection speed. As well, the mirror M1 can be substituted by any other device able to shape the intensity or phase distribution of light in order to obtain different light-delivery geometries along the taper 12 in the time instants $t_1 \ldots t_n$. To reduce the system costs, the image sensor can be substituted with a photomultiplier tubes with a pre-defined configuration of the sensible geometry, which can be single or multianode, with each of the selectively addressable sensing element being related to a specific set of $k_t$ values.

Figure 6:
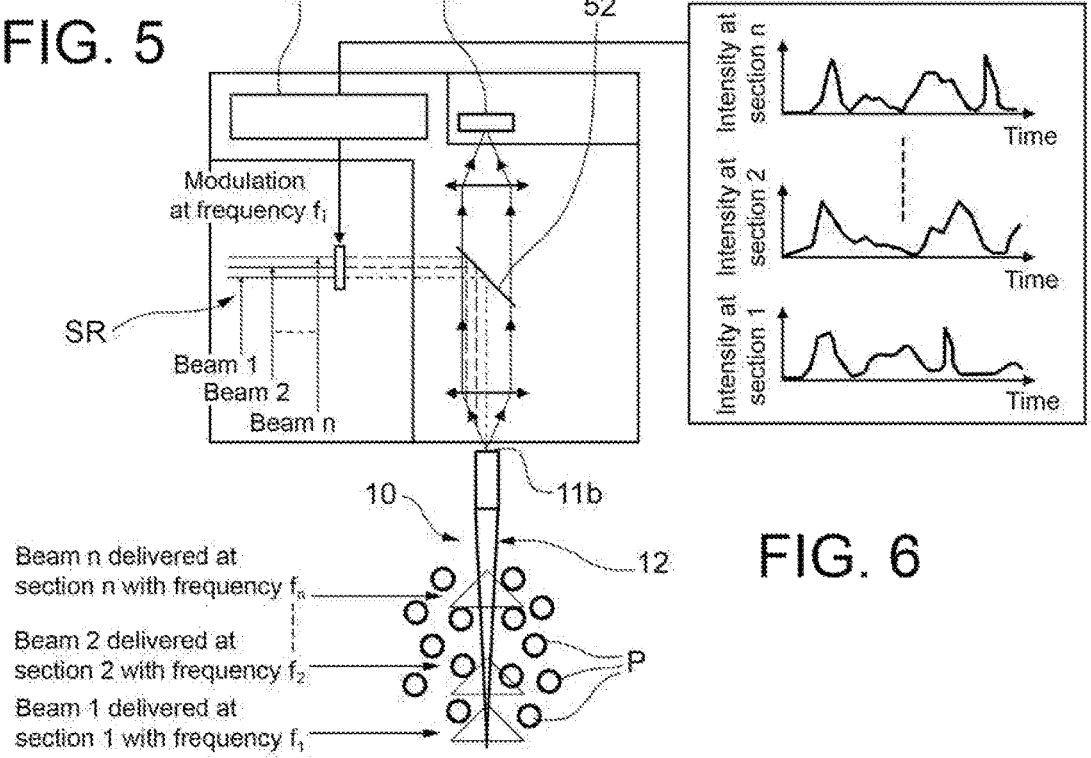
FIG. 6 shows an example configuration that allows to sample n sections of the taper simultaneously by delivering the secondary radiation at different taper sections and different modulation frequencies.

To exploit the advantage of the reduced cross-talk of FIG. 5 and to detect fluorescence at multiple sections along the taper 12 simultaneously, a third scheme is proposed in FIG. 6. n excitation beams, where n is the number of detection points expected along the taper 12, are modulated by a sinusoidal signal at the frequency $f_i$ (with $f_i \neq f_j$ for all i<n and j<n). Each beam enters into the fiber at a different angle, it is delivered at a different section along the taper 12 and therefore it modulates the fluorescence (or scattering) at the i-th section at the frequency $f_i$. The i-th taper section mainly collects the fluorescence signal at frequency and all signals are simultaneously recorded by a single photomultiplier tube 63. A control electronics 65, based on n lock-in amplifiers or equivalent systems based on digital signal processing devices, is then used to measure the intensity detected at each frequency (and therefore at each section of the taper 12) by using the modulation signals at frequency $f_i$ as reference signals. The result is a set of time traces of the collected fluorescence at different sections along the taper. This working principle is possible only because signals collected at different sections are back-propagating within different modal subsets, and therefore cross-talk between photons collected at different frequencies is reduced at minimum. As well, the single anode PMT can be substituted by a multi anode PMT. If the far field detection path shown in FIGS. 4 and 5 is implemented to image different $k_t$ values on different anodes of the PMT, also all photons generated close to the section i and collected at the section j will not be mistaken as having been generated close to section j, since the signal will be modulated at frequency $f_i$ and not $f_j$. The system in FIG. 6 is described by using sample sinusoidal signal, but the general principle can be simply extended to more complex periodic signals, such as square, rectangular or triangular waves, with the proper detection electronics to retrieve the different harmonic content that will be therefore generated.

Figure 7:
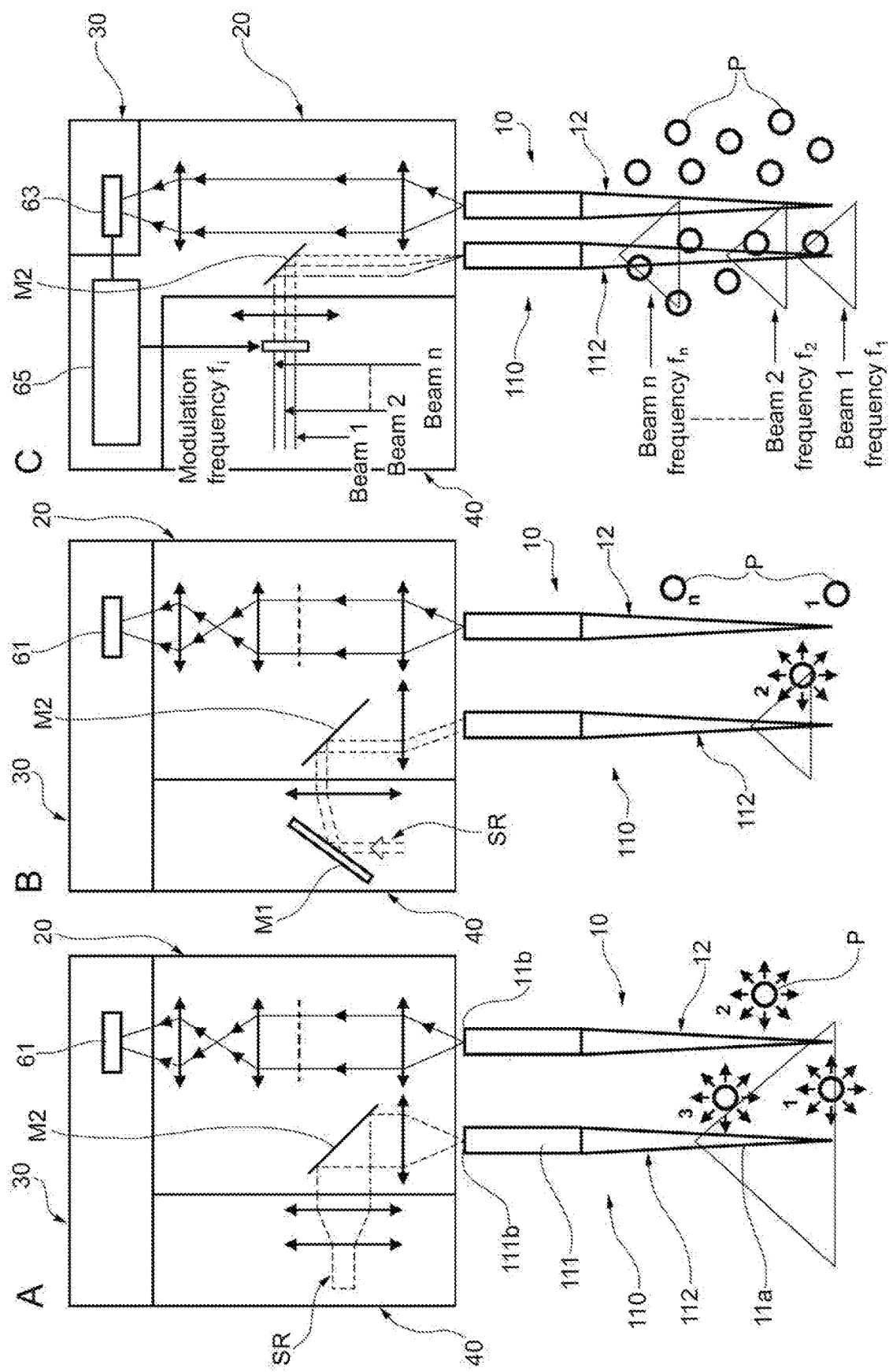
FIG. 7 shows an extension of the setups displayed in FIGS. 4, 5 and 6 to a layout in which a second tapered fiber is used to delivery the secondary radiation. Panel A refers to the optical path in FIG. 4, Panel B to the one in FIG. 5 and Panel C to the one in FIG. 6.

All layouts shown in FIGS. 4, 5 and 6 can be modified to allow the second radiation SR to be delivered following the different configurations summarized in FIG. 3. An example is displayed in FIG. 7, in which for each layout an alternative configuration using a light delivering probe 110 to deliver the secondary radiation SR into the environment is used. The light delivering probe 110 consists of a single tapered fiber constructively identical to the light collecting probe 10, and therefore comprises a waveguide 111 having a proximal end 111*a* and a distal end 111*b*, and a taper 12 formed at the proximal end 111*a* along which at least one optical windows is positioned. A fixed mirror for directing the secondary radiation SR is designated with M2. This second fiber can be used exactly with the same light delivery module of FIGS. 4-6, apart for the fact that the light delivery and collection paths will be disjoint.

Although it is not explicitly shown in the here-reported drawings, it is important to mention that any of these schemes can host photonic elements along the taper surface, such as plasmonic surfaces, nanostructures, diffraction gratings or photonic crystals, and therefore be exploited, for instance, for fiber-based depth-resolved surface plasmon enhanced raman spectroscopy (SERS).

Figure 8:
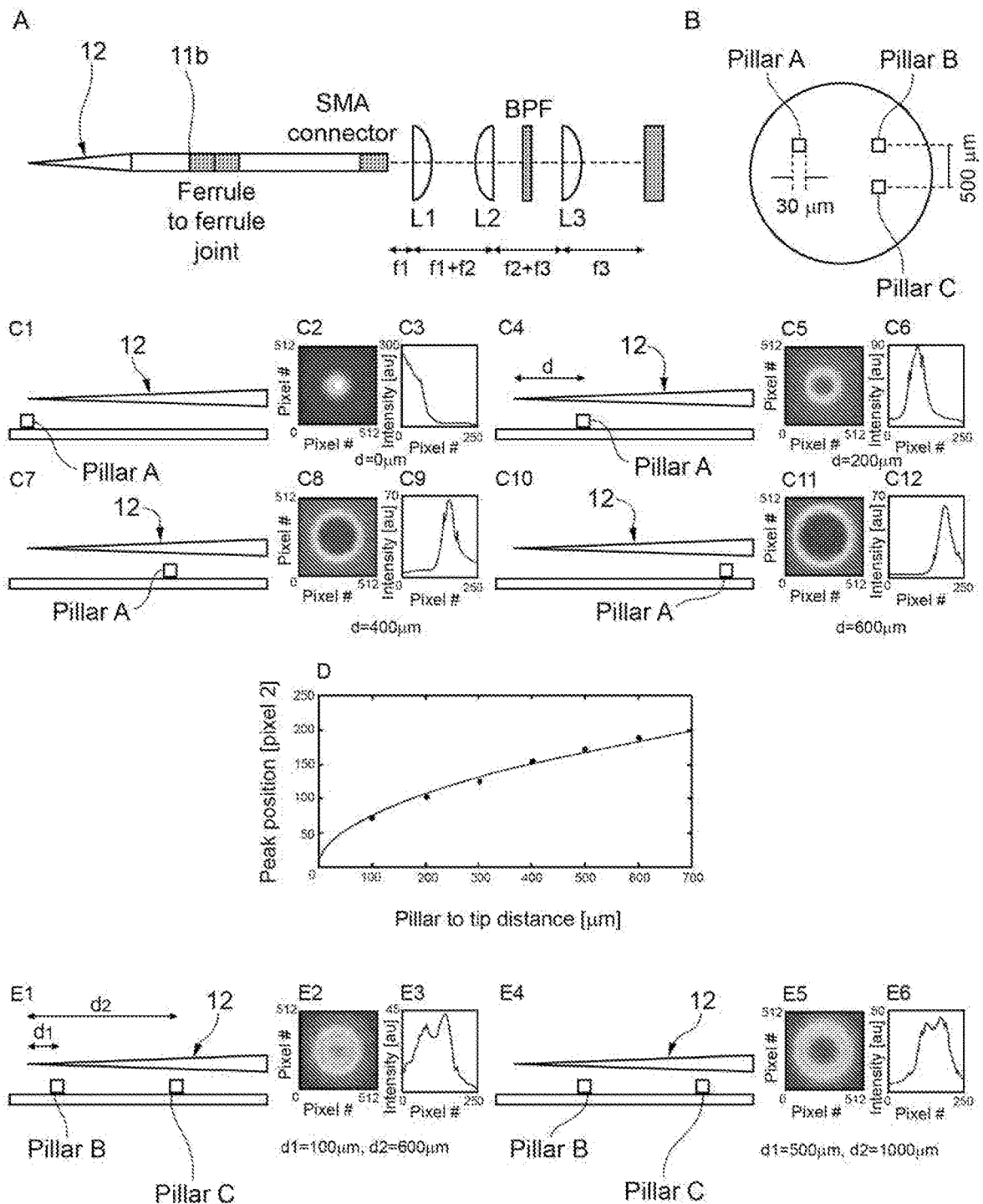
FIG. 8 shows: (Panel A) Schematic representation of an experimental system used for proof-of-concept. The tapered waveguide is connected through a patch fiber to the optical detection path composed by lenses L1, L2, L3 (with focal length f1, f2 and f3 respectively) and a sCMOS camera. (Panel B) Fluorescent sample used to test the device. Three fluorescent pillars 30 µm×30 µm×20 µm were arranged as shown, to allow for both single source (pillar A) and double source (pillars B and C) measurements. (Panel C) Summary of the single source experiment configuration. The single fluorescent pillar is placed below the device and moved along the taper as shown in Panels C1, C4, C7 and C10. The corresponding far field patterns of the detected fluorescence, recorded on the sCMOS sensor, are shown in Panels C2, C5, C8 and C11. Panels C3, C6, C9, and C12 report the radial intensity profiles for the same four different axial position of the light source, calculated as described in the main text. (Panel D) Dependence of the peak position in the radial profile from the axial position of the light source. The dots represent experimental data, while the curve represents a fit with a function proportional to the square root of the axial position of the light source. (Panel E) Summary of the double source experiment configuration. The two fluorescent pillars are placed below the device and moved along the taper as shown in Panels E1 and E4. The corresponding far field patterns of the detected fluorescence, recorded on the sCMOS sensor, are shown in panel E2 and E5. Panels E3 and E6 report the radial intensity profiles for the same two different axial position of the light sources, calculated as described in the present disclosure.

A prototype of the system was developed and tested in the laboratory. For this proof of concept, a multi-mode optical fiber (core diameter 200 µm, cladding diameter 225 µm, numerical aperture N.A. 0.39) was tapered with a taper angle of 2.9° using a heat and pull method and connectorized with a LC/PC 1.25 mm stainless steel ferrule with a total stub length of about 7 cm. The same type of optical fiber was used to realize a 1 m long patch cable to interconnect the tapered fiber to the optical detection system, with a LC/PC 1.25 mm stainless steel ferrule on the fiber side and a SMA905 stainless steel connector on the detection end. A schematic representation of this configuration is shown in FIG. 8.A, which implements the conceptual example of FIG. 4. The optical detection system consists of three lenses projecting the far-field pattern of the fiber emission over a sCMOS camera: lens L1 (focal length f1=4.6 mm) creates the far-field pattern, while lenses L2 (focal length f2=30 mm) and L3 (focal length f3=100 mm) act as an afocal magnifier, with the purpose to exploit the whole sensor area of the sCMOS camera and to allow for detection of light travelling inside the waveguide at the maximum sustained numerical aperture.

With the goal to prove the ability of the tapered fiber to gather light from a fluorescent medium and discriminate the position of light sources along the waveguide axis, a test sample with 30 μm×30 μm×20 μm (length×width×height) fluorescent pillars on a microscope coverslip was used to simulate the presence of light emitting sources along the taper (FIG. 8.B). Two different arrangements of the pillars on the sample surface were fabricated to allow for both single (pillar A in FIG. 8) and double (pillars B and C in FIG. 8.B) source test. In both cases, the fiber was positioned above the pillar(s) at a distance of 300 μm from the sample substrate (see FIG. 8.C1, C4, C7, C10, E1 and E4). The pillars were moved at different positions with respect to the taper tip to test the response of the system for different spatial distribution of the light sources. An external 473 nm fiber coupled laser source was used to excite the fluorescence of the pillars, implementing the conceptual design in FIG. 3B. The bandpass filter shown in FIG. 8.A prevents 473 nm photons to reach the sCMOS camera, and only light in the spectral interval 500 nm-550 nm was detected. In order to get rid of the contribution to the detected signal from the fiber autofluorescence, a reference for background subtraction in presence of the light emitted by the fiber coupled laser without fluorescent pillar was considered.

Images collected by the camera resulted in intensity rings with different diameters depending on the position of the fluorescent pillar along the taper, displayed in the case of a single-source experiment in FIG. 8.C for different positions of pillar A along the taper. To quantitatively estimate the light source position, detected images were post-processed in order to improve the signal to noise ratio and to extract the essential information. After a bi-dimensional moving average filtering, the image was expressed in a polar coordinate reference with the origin in the center of the sensor. For each value of the radial coordinate an average of the image intensity value along the whole circumference was performed. Therefore, dependence of the data from the angular coordinate is compressed and the 2D image is reduced to a single variable function of the radial coordinate only. Since collection of data with a circular symmetry is expected, the azimuthal averaging process lead to an increase of the signal to noise ratio with no deterioration of the information contained in the image recorded by the camera.

FIG. 8.C shows the recorded far field patterns (panels C2, C5, C8 and C11) and the corresponding normalized radial intensity averages (panels C3, C6, C9 and C12) for four different axial positions of a single pillar below the tapered fiber (panels C1, C4, C7 and C10). The dependence of the intensity peak position from the light source position (tip-pillar distance is referred to as d, defined in panel C4) is plotted in FIG. 8.D. The blue dots represent experimental data, while the overlaid red curve shows that a function proportional to the square root of d can be used to fit the data and, therefore, used to relate the intensity peak position to the actual position of the light source along the taper axis.

The presence of two pillar sources along the tapered fiber at the same time unveils the ability of the device to distinguish between two sources placed 500 μm far one from the other, as shown in FIG. 8.E. Depending on the overall structural and optical properties of the taper (numerical aperture of the non-taper fiber region, taper angle, eventual metal masking) this resolution can be improved or reduced, depending on the specific application.

Figure 9:
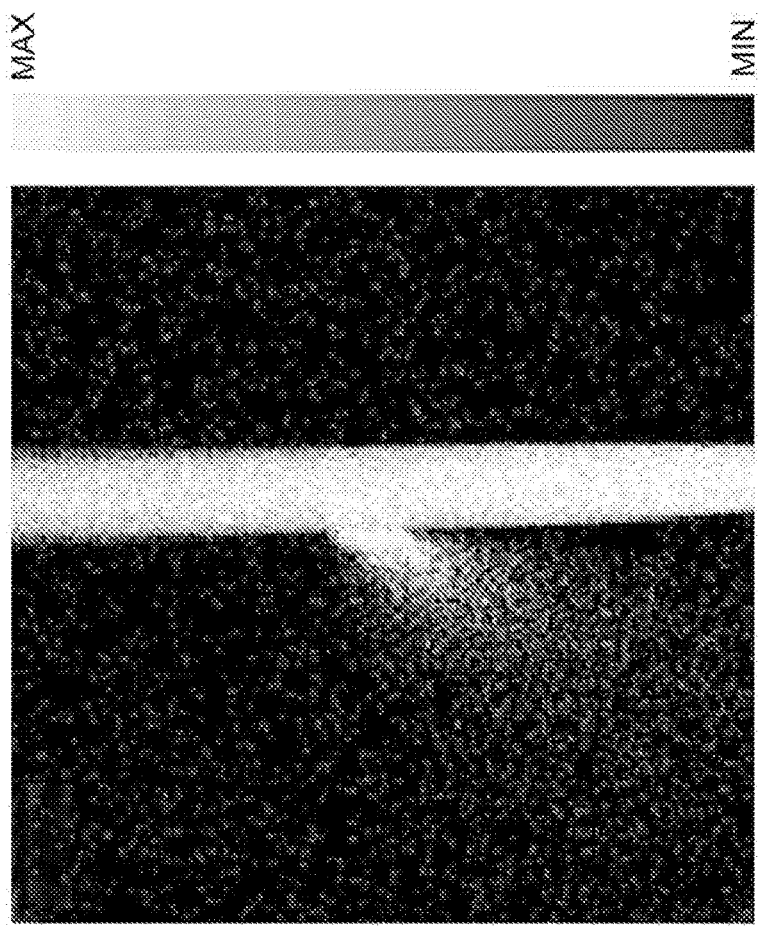
FIG. 9 shows: (Panel A) Schematic representation of the measurement setup. A metal coated fiber with a 30 µm×30 µm optical aperture realized on the taper is immersed into a fluorescent solution and placed below the objective of a two-photon excitation microscope. The laser beam from the microscope is used to excite fluorescence light inside the solution and the photons collected by the fiber are detected using a photomultiplier tube. (Panel B) Bi-dimensional slice of the 3D collection diagram measured using the system depicted in Panel A. The gray area represents the optical fiber (collected by the microscope), while the green signal is the light intensity detected by the point detector for each pixel of the scan at the distal end of the fiber (PMT in panel A). Scalebar is 50 µm.
Figure 9:
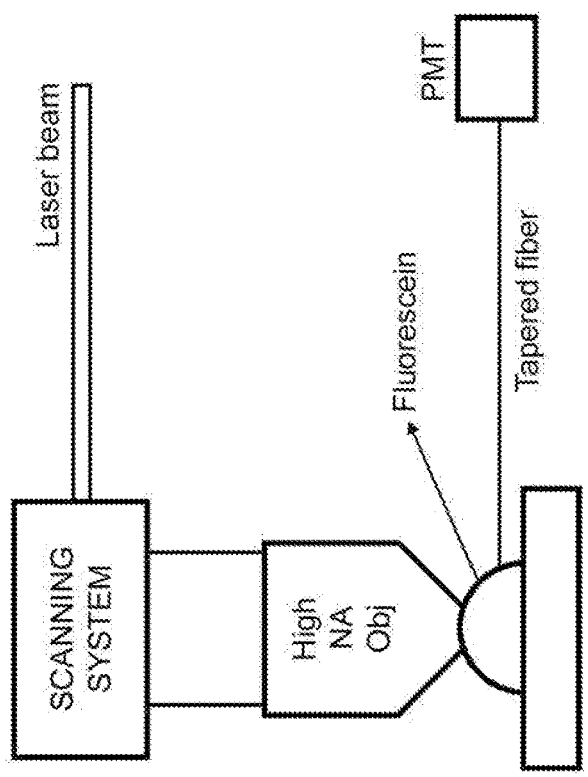

Qualitative information on the volume in which the device is sensitive to light radiation were extracted using a two-photon laser scanning microscopy system, as schematized in FIG. 9.A. In this case this is shown for a device with a discrete number of input positions along the taper realized through a metal mask, a configuration already shown in FIG. 2.B. For this experiment, a device with a metal coating all around the taper with exception for a 30 μm×30 μm window was immersed in a green-fluorescent bath (composed by a PBS:fluorescein solution) and a near infrared femtosecond-pulsed laser was used as a secondary radiation to excite fluorescence around the fiber. This excitation beam was moved in a raster scan around and along the fiber taper. Light generated by the two photon beam was collected through the fiber by a photomultiplier tube placed at the fiber output synchronously with the raster scanner. The result of the measurement is a 3D intensity map where each pixel represents the light intensity collected through the fiber taper when the beam was exciting fluorescence in that specific pixel. Therefore, the intensity map represents a collection efficiency diagram. FIG. 9B reports a 2D slice of this collection efficiency diagram, in which the lighter gray area represents the tapered fiber while the gray plume on the left side of the fiber is the detected light intensity. It can be clearly seen that the device is sensitive to light emitted in the proximity of the collection window, and the collection efficiency fade out as the distance between the window and the light source increases, as expected.

Even though the previous discussion was focused on tapered and uncoated fiber or metal-coated tapered fiber with a single square window, both the procedures are general and can be extended to devices with more than one window or with complex optical element realized on them.

The invention claimed is:

1. A system for light collection through a probe implanted in a tissue, said system including
   a light collecting probe comprising a waveguide formed by a single optical fiber and having a proximal end and a distal end, said proximal end being formed with a taper along which at least one optical window is positioned, wherein said single optical fiber is capable of sustaining a plurality of guided modes of light propagating in said single optical fiber, and wherein light entering at an axial section of the taper generates a respective subset of guided modes of said plurality of guided modes defined by a diameter of the single optical fiber at said axial section, said subset of guided modes propagating toward the distal end of the waveguide and generating a respective radial light intensity profile at the distal end of the waveguide;
   a demultiplexer configured to receive a plurality of said radial light intensity profiles provided by the light collecting probe and associated to a plurality of respective light input points along the taper, said demultiplexer being configured to discriminate said radial light intensity profiles based on their modal content of origin; and
   a detector configured to collect a far-field pattern of the discriminated radial light intensity profiles provided by the demultiplexer.

2. The system of claim 1, wherein the taper comprises an optical window in which multiple light input points are continuously distributed over the optical window.

3. The system of claim 1, wherein the taper comprises multiple optical windows discretely distributed over the taper.

4. The system of claim 1, further comprising a light delivery element configured to introduce a secondary radiation into the tissue, the light entering the taper being emitted or scattered by the tissue as a response to the secondary radiation.

5. The system of claim 4, wherein the light delivery element comprises multiple light generators integrated along the light collecting probe.

6. The system of claim 4, wherein the secondary radiation is carried along the waveguide, and wherein at least one axial section of the taper radiates a specific subset of propagating modes of the carried secondary radiation defined by the diameter of the single optical fiber at said at least one axial section.

7. The system of claim 4, wherein the light delivery element comprises a light delivering probe distinct from the light collecting probe and comprising a waveguide formed by a single optical fiber and having a proximal end and a distal end, said proximal end being formed with a taper along which at least one optical window is positioned, and wherein at least one axial section of the taper radiates a specific subset of propagating modes of the carried secondary radiation defined by the diameter of the single optical fiber at said at least one axial section.

8. The system of claim 6 wherein the light delivery element is configured to inject the secondary radiation into the distal end of the light collecting probe with an adjustable input angle ($\theta$).

9. The system of claim 6, wherein the light delivery element is configured to provide a plurality of beams of the secondary radiation, said beams being modulated with different modulation frequencies, wherein the light delivery element is configured to inject said beams into the distal end of the light collecting probe with different input angles, and wherein the demultiplexer is configured to discriminate the radial light intensity profiles provided by the distal end of the light collecting probe based on their modulation frequencies.

10. The system of claim 1, wherein the detector comprises a sensor configured to collect a far-field pattern of the output of the light collecting probe.

11. A method for light collection through a light collecting probe pre-implanted in a tissue, said light collecting probe comprising a waveguide formed by a single optical fiber and having a proximal end and a distal end, said proximal end being formed with a taper along which at least one optical window is positioned, wherein said single optical fiber is capable of sustaining a plurality of guided modes of light propagating in said single optical fiber, wherein said method comprises
collecting light through the light collecting probe, wherein light entering at an axial section of the taper generates a respective subset of guided modes of said plurality of guided modes defined by a diameter of the single optical fiber at said axial section, said subset of guided modes propagating toward the distal end of the waveguide and generating a respective radial light intensity profile at the distal end of the waveguide;
receiving a plurality of said radial light intensity profiles provided by the light collecting probe and associated to a plurality of respective light input points along the taper, and discriminating said radial light intensity profiles based on their modal content of origin; and
collecting a far-field pattern of the discriminated radial light intensity profiles.

12. The method of claim 11, wherein detecting the discriminated outputs comprises simultaneously detecting a plurality of discriminated outputs associated to respective axial sections of the taper.

13. The method of claim 11, wherein detecting the discriminated outputs comprises detecting, at different time instants, discriminated outputs associated to respective axial sections of the taper.

14. The method of claim 11, further comprising introducing a secondary radiation into the tissue, the light entering the taper being emitted or scattered by the tissue as a response to the secondary radiation.

15. The method of claim 14, wherein the secondary radiation is introduced through the light collecting probe.

16. The method of claim 14, wherein the secondary radiation is introduced through a light delivering probe distinct from the light collecting probe and comprising a waveguide formed by a single optical fiber and having a proximal end and a distal end, said proximal end being formed with a taper along which at least one optical window is positioned, and wherein at least one axial section of the taper radiates a specific subset of propagating modes of the carried secondary radiation defined by the diameter of the single optical fiber at that said at least one axial section.

17. The method of claim 15, wherein the secondary radiation is injected into the distal end of the light collecting probe with an adjustable input angle ($\theta$).

18. The method of claim 15, wherein introducing the secondary radiation comprises
generating a plurality of beams of the secondary radiation, said beams being modulated with different modulation frequencies,
injecting said beams into the distal end of the light collecting probe with different input angles ($\theta$), and
discriminating the radial light intensity profiles provided by the distal end of the light collecting probe based on their modulation frequencies.

19. The system of claim 7 wherein the light delivery element is configured to inject the secondary radiation into the distal end of the light delivering probe with an adjustable input angle ($\theta$).

20. The system of claim 7, wherein the light delivery element is configured to provide a plurality of beams of the secondary radiation, said beams being modulated with different modulation frequencies, wherein the light delivery element is configured to inject said beams into the distal end of the light delivering probe with different input angles, and wherein the demultiplexer is configured to discriminate the radial light intensity profiles provided by the distal end of the light delivering probe based on their modulation frequencies.

21. The method of claim 16, wherein the secondary radiation is injected into the distal end of the light delivering probe with an adjustable input angle ($\theta$).

22. The method of claim 16, wherein introducing the secondary radiation comprises
generating a plurality of beams of the secondary radiation, said beams being modulated with different modulation frequencies,
injecting said beams into the distal end of the light delivering probe with different input angles ($\theta$), and
discriminating the radial light intensity profiles provided by the distal end of the light delivering probe based on their modulation frequencies.

* * * * *